United States Patent [19]

Narabe et al.

[11] Patent Number: 5,519,159
[45] Date of Patent: May 21, 1996

[54] PHOSPHATIDYLCHOLINE WITH HIGH OXIDATIVE STABILITY AND PROCESS FOR ITS PREPARATION

[75] Inventors: Hitoshi Narabe, Hino; Hideaki Kobayashi; Mineo Hasegawa, both of Hachioji, all of Japan

[73] Assignee: Kewpie Kabushiki Kaisha, Tokyo, Japan

[21] Appl. No.: 411,672

[22] PCT Filed: Oct. 12, 1993

[86] PCT No.: PCT/JP93/01462

§ 371 Date: Apr. 14, 1995

§ 102(e) Date: Apr. 14, 1995

[87] PCT Pub. No.: WO94/09015

PCT Pub. Date: Apr. 28, 1994

[30] Foreign Application Priority Data

Oct. 15, 1992 [JP] Japan ..................................... 4-277533

[51] Int. Cl.⁶ ....................................................... C07F 9/10
[52] U.S. Cl. .............................................. 558/169; 558/146
[58] Field of Search ...................................... 558/169, 146

[56] References Cited

U.S. PATENT DOCUMENTS

| | | | |
|---|---|---|---|
| 4,857,236 | 8/1989 | Günther | 558/146 X |
| 4,983,327 | 1/1991 | Günther | 558/146 X |

*Primary Examiner*—Johann Richter
*Assistant Examiner*—Michael G. Ambrose
*Attorney, Agent, or Firm*—Oblon, Spivak, McClelland, Maier & Neustadt

[57] ABSTRACT

Disclosed are a phosphatidylcholine excellent in oxidation stability, in which the ratio of the total weight of palmitoyl-linoleoyl-glycerophosphocholine (PLPC) and palmitoyl-oleoyl-glycerophosphocholine (POPC) to the total weight of stearoyl-linoleoyl-glycerophosphocholine (SLPC) and stearoyl-oleoyl-glycerophosphocholine (SOPC) is 4.5 or less, the PLPC, POPC, SLPC and SOPC being molecular species constituting the phosphatidylcholine, and in which the electric conductivity of a 5 wt. % suspension of the phosphatidylcholine in distilled water is 100 µS/cm or less; and a process for producing the same.

2 Claims, 1 Drawing Sheet

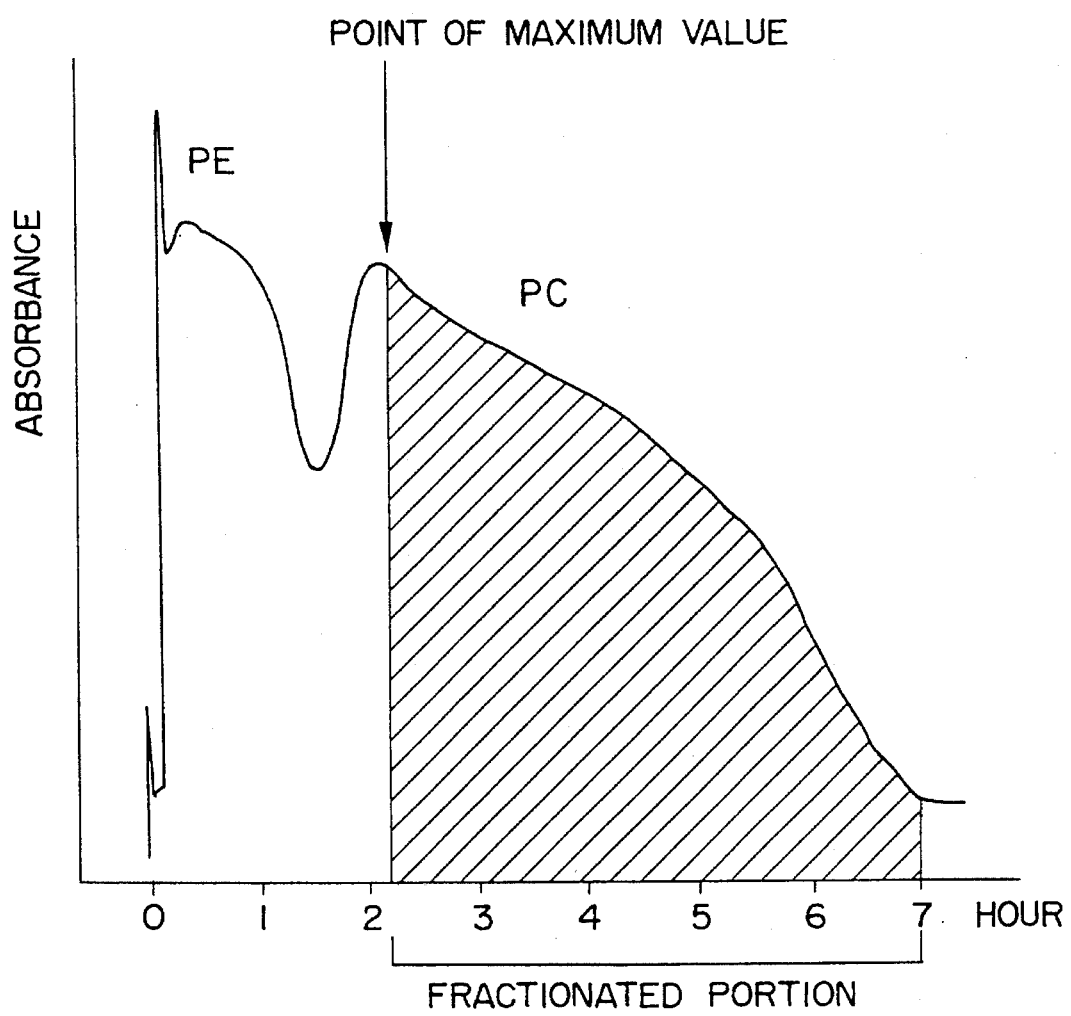
F I G. 1 ns stage filing under 35 U.S.C.
PHOSPHATIDYLCHOLINE WITH HIGH OXIDATIVE STABILITY AND PROCESS FOR ITS PREPARATION This application is a national stage filing under 35 U.S.C. § 371 that is based upon PCT International Application No. PCT/JP93/01462, which was filed on Oct. 12, 1993.

TECHNICAL FIELD

The present invention relates to a phosphatidylcholine excellent in oxidation stability, and a process for producing the same.

BACKGROUND ART

In general, phosphatidylcholines contain as a constituent fatty acid thereof an unsaturated fatty acid such as oleic acid, linoleic acid, linolenic acid, docosahexaenic acid or arachidonic acid, so that they have the property of being readily oxidized. In particular, when phosphatidylcholines are purified to high purity, they are separated from neutral lipids or proteins which have existed as impurities and acted just like protective layers, and directly exposed to oxygen in the air, so that they are oxidized more easily.

For this reason, there has been made an effort to prevent phosphatidylcholines from being oxidized, e.g., during storage. Generally, they are stored in a dark and cool place or in an inert gas atmosphere; an antioxidant such as vitamin E is added to them; or an unsaturated bond contained in them is converted into a saturated bond by hydrogenation.

Phosphatidylcholines which are purified to high purity are often used for cosmetics, drugs or the like. In such cases, they are usually utilized as liposomes, emulsifying agents or the like. It has been known that, in such cases, the smaller is the amount of impurities such as inorganic salts and free amino acids, the better are the products obtained. (See, for example, Japanese Laid-Open Patent Publication No. 3115/1989.)

However, although storage in a dark and cool place or in an inert gas atmosphere is effective for phosphatidylcholines prepared, it is impractical and almost impossible for those products such as cosmetics and drugs which are produced by using the phosphatidylcholines.

Further, the addition of an antioxidant to phosphatidylcholines is unfavorable when their use in cosmetics, drugs, foods or the like is taken into consideration. There is also a case where an antioxidant cannot be added.

Furthermore, in order to conduct a hydrogenation treatment, it is necessary to additionally provide a step for this purpose.

In addition, the stability of liposomes or emulsified products obtained by using phosphatidylcholines is reduced when the phosphatidylcholines are oxidized. Moreover, the phosphatidylcholine oxides also bring about the problem of toxicity for the body or the like.

It has thus been general rules that purified phosphatidylcholines should be stored in a dark and cool place immediately after the preparation thereof and used for producing desired products as soon as possible, and that the products obtained should also be consumed in a short period of time.

Under these circumstances, it is now acknowledged that the development of phosphatidylcholines which are per se excellent in oxidation stability is strongly required.

Therefore, an object of the present invention is to provide phosphatidylcholines excellent in oxidation stability and thus can meet the above requirement.

SUMMARY OF THE INVENTION

We have made extensive studies in order to attain the aforementioned object, and finally accomplished the present invention.

The present invention is to provide a phosphatidylcholine characterized in that the ratio of the total weight of palmitoyl-linoleoyl-glycerophosphocholine (PLPC) and palmitoyl-oleoyl-glycerophosphocholine (POPC) to the total weight of stearoyl-linoleoyl-glycerophosphocholine (SLPC) and stearoyl-oleoyl-glycerophosphocholine (SOPC) is 4.5 or less, the PLPC, POPC, SLPC and SOPC being molecular species constituting the phosphatidylcholine, and that the electric conductivity of a 5 wt. % suspension of the phosphatidylcholine in distilled water is 100 µS/cm or less.

BRIEF DESCRIPTION OF THE DRAWING

FIG. 1 is a graph showing the ultraviolet absorption chromatogram of the eluate obtained in Example 1 of the present invention.

BEST MODE FOR CARRYING OUT THE INVENTION

The phosphatidylcholine, the object substance of the present invention, is, in general, represented by the following structural formula:

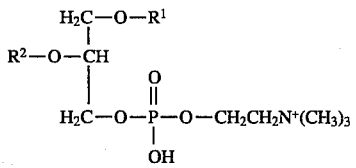

wherein $R^1$ and $R^2$ represent an acyl group.

In the present invention, the term "molecular species" means an individual compound which is given by changing the combination of the acyl groups bonded. Therefore, the molecular species which constitutes a phosphatidylcholine is an individual phosphatidylcholine whose structure is determined by assigning specific groups to the acyl groups contained in this phosphatidylcholine and indicated by $R^1$ and $R^2$ in the above formula.

In the present invention, SLPC is a phosphatidylcholine having the above formula in which the acyl group $R^1$ is a stearic acid residue, and the acyl group $R^2$ is a linolenic acid residue.

SOPC is a phosphatidylcholine having the above formula in which the acyl group $R^1$ is a stearic acid residue, and the acyl group $R^2$ is an oleic acid residue.

PLPC is a phosphatidylcholine having the above formula in which the acyl group $R^1$ is a palmitic acid residue, and the acyl group $R^2$ is a linolenic acid residue.

POPC is a phosphatidylcholine having the above formula in which the acyl group. $R^1$ is a palmitic acid residue, and the acyl group $R^2$ is an oleic acid residue.

According to the present invention, the phosphatidylcholine of the present invention is one having a ratio (the weight of PLPC+the weight of POPC)/(the weight of SLPC+the weight of SOPC) of 4.5 or less. When this weight ratio is higher than this value, i.e., 4.5, it is difficult to obtain a phosphatidylcholine having oxidation stability.

Furthermore, according to the present invention, the phosphatidylcholine of the present invention is one having an electric conductivity of 100 μS/cm or less in a 5 wt. % suspension of the phosphatidylcholine in distilled water. It is noted that all the values of the electric conductivity shown herein were obtained by a measurement at 25° C. When this electric conductivity is higher than 100 μS/cm, it is difficult to obtain a phosphatidylcholine having oxidation stability.

The phosphatidylcholine of the present invention is thus characterized in that the weight ratio (PLPC+ POPC)/ (SLPC+SOPC) is 4.5 or less, and that the electric conductivity determined under-the aforementioned conditions is 100 μS/cm or less. As will be clear from the results of the change in peroxide value with an elapse of time during storage obtained in the Test Example which will be described later, the phosphatidylcholine is essentially required to have both the above-described weight ratio among the molecular species and the above-described electric conductivity from the viewpoint of oxidation stability.

It is not necessary that the phosphatidylcholine of the present invention be a pure product as long as it has the above-described requirements. For instance, the phosphatidylcholine may contain neutral lipids or cholesterol which is generally contained in conventional phosphatidylcholines extracted from natural products, or an extremely small amount of other phospholipids which can be contaminated. However, since the phosphatidylcholine is a main component of the final product, it is preferable that at least 70% or more of the total components of the phosphatidylcholine be contained in the final product.

The phosphatidylcholine of the present invention can generally be produced in the following manner.

A lipid composition comprising a phosphatidylcholine is firstly prepared. Examples of such a lipid composition include -those obtained by extraction by a conventional method from known phospholipid-containing materials such as plant seeds, yolks, brains, internal organs or bacteria, and those obtained by various synthesis methods. For example, an organic solvent in which the phosphatidylcholine is readily dissolved, such as dichloromethane or an alcohol, is added to a dried and pulverized phospholipid-containing material, and the mixture is stirred. Solid substances are removed from the mixture to obtain a liquid phase, which is washed with an organic solvent in which the phosphatidylcholine is hardly dissolved, such as acetone. The solvent is then removed from a precipitate. A lipid composition containing the phosphatidylcholine can thus be obtained. This lipid composition may be either one consisting of the phosphatidylcholine only, or one further containing lipids other than the phosphatidylcholine.

Subsequently, the lipid composition thus obtained is treated by using column chromatography, and the portion of the phosphatidylcholine of the present invention is fractionated and collected.

A typical method for fractionating and collecting the phosphatidylcholine of the present invention, in which liquid column chromatography is used as the column chromatography, will now be explained.

It is preferable that the lipid composition obtained in the above-described manner contain, in general, 5% or more of the phosphatidylcholine. It is more preferable to control, depending upon the desired final product, the phosphatidylcholine content of the lipid composition prior to the chromatographic treatment. For example, it is preferable to control the phosphatidylcholine content of the lipid composition to be 20% or more in order to obtain a high-purity product.

Liquid column chromatography may be conducted in accordance with a conventional technique. However, in the case where the phosphatidylcholine collected is intended to be used for drugs, cosmetics, foods or the like, it is better to use, as a mobile phase, a solvent which is safe for the human body.

A case where silica gel is used as the filler and an alcohol and water are used as the mobile phase solvent will now be explained as an example.

Regarding the silica gel, there is no particular limitation on the type thereof. It is however desirable to use silica gel which is obtained from silicon tetrachloride or sodium silicate and in which silicic acids are three-dimensionally polymerized. Silica gel having fine pores with a diameter of 10 to 2,000 Angstroms, referred to as entirely porous silica, is preferable as the silica gel of the above type. Specific examples of such silica gel include entirely porous spherical silica gel having a particle diameter of 3 to 50 μm, entirely porous pulverized silica gel having a particle diameter of 5 to 350 μm, and the like.

Any alcohol can be used as the mobile phase solvent as long as it can be used for it. However, a solvent mixture of an alcohol having 4 or less carbon atoms and water is preferable from the viewpoint of the solubility of the phosphatidylcholine. Specific examples of such mobile phase solvent include methanol, ethanol, propanol, butanol, and structural isomers thereof. From the viewpoint of the safety of the human body, ethanol is used. The preferable mixing ratio of an alcohol to water is approximately from 99:1 to 50:50 by volume. This is because when the proportion of the alcohol is either higher or lower than this, it tends to be difficult to obtain the phosphatidylcholine of the present invention.

The detection of the phosphatidylcholine eluted from a column may be conducted by a conventionally known method such as the ultraviolet absorption method or the ultrasonic measurement method. The eluate is gathered (fractionated and collected) after the time when the chromatogram of the phosphatidylcholine fraction obtained as a result of the detection shows a maximum value, and the solvent is removed from the eluate by a conventional method. The phosphatidylcholine of the present invention can thus be obtained. It is noted that any portion may be collected as long as the portion is obtained after the time when the maximum value is shown and further as long as the phosphatidylcholine is detected in the portion.

In order to increase the content of the thus-obtained phosphatidylcholine itself, that is, in order to increase the purity of the phosphatidylcholine of the present invention, the step of the above-described chromatography may be repeated, or purification may be conducted by a conventional method by using an organic solvent such as an alcohol or acetone.

As will be clear from the results obtained in the Test Example which will be described later, the phosphatidylcholine of the present invention thus obtained is per se excellent in oxidation stability.

The present invention will now be explained more specifically by referring to the following Examples and Test Example. It is noted that all percentages and ratios used in the present invention are by weight unless otherwise specified.

EXAMPLE 1

150 g of purified yolk phospholipid (containing approximately 80% of a phosphatidylcholine) having the following composition was dissolved in 300 ml of a 92 vol. % aqueous ethanol solution to obtain a sample. High-performance liquid column chromatography was conducted under the following conditions.

(Composition of Phospholipid, unit=%)
Phosphatidylcholine 81.6
Phosphatidyl ethanolamine 16.3
Cholesterol 1.1
Sphingolipid 0.8
Lysophospholipid 0.2
(Conditions)
Column: Inside diameter 50 mm×length 1000 mm
Packing material: Silica gel (entirely porous spherical silica gel having a particle diameter of 40 to 60 μm)
Mobile phase: Ethanol/water=92/8 (v/v), 150 ml/min
Detection: Ultraviolet absorption ($\lambda$=204 nm)

The order of the elution of the phospholipids is such that the phosphatidylethanolamine (PE) is first, and the phosphatidylcholine (PC) is next to it. Therefore, while the ultraviolet absorption of the eluate delivered from the column was being measured, the collection of the eluate was started at the point at which the chromatogram of the phosphatidylcholine fraction showed a maximum value, and continued until the time when the detection of the phosphatidylcholine by ultraviolet absorption was completed. (See FIG. 1.)

The solvent components were removed from the solution collected, and the residue was dried in a vacuum drier to obtain 98.1 g of the phosphatidylcholine of the present invention.

The purity of the above-obtained phosphatidylcholine of the present invention was 99.9% as measured by the TLC-FID method (*Journal of the Japan Oil Chemistry*, 32 (10), 566–573 (1983), published by the Japan Oil Chemists' Society), provided that the conditions of the development were modified as follows.

(Conditions of Development)
Rod: Chromatorod S-111 (manufactured by Kabushiki Kaisha Yatoron)
Solvents for Development:
First development: Chloroform/methanol/water (70/30/3 v/v), 8 cm.
Second development: n-Hexane/diethyl ether/formic acid (90/10/0.1 v/v), 10 cm The composition of the four molecular species constituting the above-obtained phosphatidylcholine, PLPC, POPC, SLPC and SOPC, was determined from an RI detection chart obtained by high-performance liquid column chromatography under the following conditions of measurement. The results were as shown in Table 1 which will be given later. The (PLPC+POPC)/(SLPC+SOPC) weight ratio was obtained on the basis of the contents of the species thus determined. The results are shown in Table 2 which will be given later.

(Conditions of Measurement)
Filler: Octadecyl silica gel (inside diameter 4.6 mm×length 250 mm)
Mobile phase: Methyl alcohol/1 mM potassium phosphate buffer (pH 7.4, 93/7 v/v), 1.5 ml/min
Detection: Differential refractometer (RI)
Amount of Sample: 500 μg Further, the electric conductivity of the above-obtained phosphatidylcholine of the present invention was measured by the following method.

Distilled water was added to 1.5 g of the sample to a total weight of 30 g. The sample was dispersed in a homogenizer to prepare a 5% suspension of the sample in distilled water. The electric conductivity of this phosphatidylcholine suspension was measured by an electric conductivity meter ("Conductivity Meter DS-14" (Trademark) manufactured by Horiba, Ltd.). The results were as shown in Table 2 which will be given later.

EXAMPLE 2

250 g of yolk phospholipid (containing approximately 60% of a phosphatidylcholine) having the following composition was dissolved in absolute ethanol to a total amount of the solution of 500 ml to obtain a sample.

(Composition of Phospholipid, unit=%)
Phosphatidylcholine 62.4
Phosphatidyl ethanolamine 11.8
Neutral lipids 24.3
Sphingolipid 0.7
Lysophospholipid 0.8

High-performance liquid column chromatography was conducted under the same conditions as in Example 1, and the collection of the eluate was started at the point at which the chromatogram of the phosphatidylcholine fraction showed a maximum value, and continued until the completion of the detection of the phosphatidylcholine by ultraviolet absorption.

The solution obtained was dried in a vacuum drier to obtain 102.7 g of the phosphatidylcholine of the present invention. The purity and composition of the phosphatidylcholine were determined by the TLC-FID method employed in Example 1. The results were as follows.

(Composition of Phosphatidylcholine of the Present Invention)
Phosphatidylcholine 74.9%
Neutral lipids 24.6
Sphingolipid 0.3
Lysophospholipid 0.2

The composition of the four molecular species constituting the phosphatidylcholine obtained, and the electric conductivity thereof were determined in the same manner as in Example 1. The results were as respectively shown in Tables 1 and 2 which will be given later.

Samples 1 to 7 of phosphatidylcholines to be used as control to the phosphatidylcholines of the present invention in the Test Example, which will be described later, were respectively prepared or provided in the following manner. With respect to the control phosphatidylcholines obtained, the composition of the four molecular species constituting the phosphatidylcholine and the electric conductivity were determined in the same manner as in Example 1. The results are respectively shown in Tables 1 and 2 which will be given later.

CONTROL SAMPLE 1

The same yolk phospholipid as in Example 1 was subjected to chromatography under the same conditions as in Example 1.

A portion at which the phosphatidyl ethanolamine overlaps the phosphatidylcholine fraction was confirmed in advance by means of thin layer chromatography. The collection of the eluate was started when the elution of the phosphatidyl ethanolamine was completed (before the chromatogram of the phosphatidylcholine fraction showed a maximum value), and continued until the completion of the detection of the phosphatidylcholine by ultraviolet absorption.

The solvent components were removed from the solution collected, and the precipitate obtained was dried in a vacuum drier to obtain 110.4 g of a phosphatidylcholine (purity: 98.2%). (The purity was measured in accordance with the method employed in Example 1 as in all succeeding Samples.)

CONTROL SAMPLE 2

The phosphatidylcholine was purified by the method described in Japanese Patent Publication No. 16/1985.

Namely, 50 ml of methanol was added to 5 g of the same purified yolk phospholipid as in Example 1 to obtain a solution. To this was added a solution obtained by dissolving 0.5 g of magnesium sulfate in 3 ml of distilled water. After the mixture was stirred and then left standing, only the supernatant of the mixture was collected. The solvent was removed under reduced pressure to obtain a purified phosphatidylcholine (purity: 97.2%).

CONTROL SAMPLE 3

An electric-conductivity-controlling solution containing potassium chloride, sodium chloride, calcium chloride, magnesium chloride and iron chloride each at a concentration of 10 mM, was prepared.

Separately, distilled water was added to 1.5 g of the phosphatidylcholine obtained in Example 1 to a total weight of 30 g. Thereafter, the phosphatidylcholine was dispersed in a homogenizer to prepare a 5% suspension of the phosphatidylcholine in distilled water.

To this phosphatidylcholine suspension was added 0.3 ml of the electric-conductivity-controlling solution, and the mixture was then lyophilized. A phosphatidylcholine with a controlled electric conductivity was thus produced.

CONTROL SAMPLE 4

A phosphatidylcholine with a controlled electric conductivity was produced in the same manner as in the case of Control Sample 3 except that 0.5 ml of the electric-conductivity-controlling solution was added.

CONTROL SAMPLE 5

A phosphatidylcholine with a controlled electric conductivity was produced in the same manner as in the case of Control Sample 3 except that 1 ml of the electric-conductivity- controlling solution was added.

CONTROL SAMPLE 6

A commercially available purified yolk phosphatidylcholine ("Coatsome NC-10S" (Trademark) manufactured by Nippon Oils & Fats Co., Ltd., purity: approximately 99%) was provided.

CONTROL SAMPLE 7

A commercially available purified yolk phosphatidylcholine ("L-α-Phosphatidylcholine Type X1-E" (Trademark) manufactured by SIGMA Co., Ltd., purity: approximately 99%), of which manufacturer is different from that of Control Sample 6, was provided.

TABLE 1

| Phosphatidylcholine | PLPC | POPC | SLPC | SOPC |
| --- | --- | --- | --- | --- |
| Example 1 | 1.05 | 2.00 | 0.50 | 0.45 |
| Example 2 | 1.30 | 2.55 | 0.70 | 0.55 |
| Control Sample 1 | 1.05 | 1.85 | 0.25 | 0.25 |
| Control Sample 2 | 1.60 | 1.90 | 0.35 | 0.25 |
| Control Sample 6 | 1.60 | 2.05 | 0.45 | 0.25 |
| Control Sample 7 | 1.65 | 2.75 | 0.45 | 0.45 |

Note 1: The numerical values in the Table indicate the heights (cm) of the respective molecular species on the chart.
Note 2: The compositions of the molecular species of Control Samples 3, 4 and 5 are the same as that of Example 1.

TEST EXAMPLE

With respect to the phosphatidylcholines of the present invention obtained in Examples 1 and 2, and the phosphatidylcholines of Control Samples 1 to 7, a change in peroxide value (POV) with an elapse of time during storage was determined in the following manner under the following conditions. The results are shown in the following Table 2.

(Storage Conditions)

Each sample was placed on a Petri dish, and left standing without a cover in a dark thermostatic chamber at 20° C.

(Measurement of POV)

The measurement was conducted in accordance with the method described on the first and second pages of 2.4.12-71 of "Standard Assay Methods of Oils and Fats" published by the Japan Oil Chemists' Society on Jan, 30, 1972.

The results shown in Table 2 demonstrate that only those phosphatidylcholines which fulfill both the weight ratio and the electric conductivity requirements, that is, only those which are equivalent to the phosphatidylcholines of the present invention have remarkably high oxidation stability.

TABLE 2

| Phosphatidyl-choline | Molecular Species | | Electric Conductivity | | Peroxide Value (mcq/kg) | | | | Overall |
| --- | --- | --- | --- | --- | --- | --- | --- | --- | --- |
| | Weight Ratio | Evaluation | μS/cm | Evaluation | Day 0 | Day 7 | Day 35 | Day 70 | Evaluation |
| Example 1 | 3.2 | o | 65.5 | o | 0 | 0 | 0 | 10 | o |
| Example 2 | 3.1 | o | 19.8 | o | 0 | 0 | 0 | 12 | o |
| Control Sample 1 | 5.8 | x | 24.4 | o | 0 | 91 | 420 | — | x |
| Control Sample 2 | 5.8 | x | 430.0 | x | 0 | 380 | — | — | x |
| Control Sample 3 | 3.2 | o | 125.6 | x | 0 | 40 | 192 | — | x |
| Control | 3.2 | o | 164.8 | x | 0 | 150 | — | — | x |

TABLE 2-continued

| Phosphatidyl-choline | Molecular Species | | Electric Conductivity | | Peroxide Value (mcq/kg) | | | | Overall Evaluation |
|---|---|---|---|---|---|---|---|---|---|
| | Weight Ratio | Evaluation | μS/cm | Evaluation | Day 0 | Day 7 | Day 35 | Day 70 | |
| Sample 4 Control | 3.2 | o | 265.2 | x | 0 | 280 | — | — | x |
| Sample 5 Control | 5.2 | x | 12.5 | o | 0 | 0 | 76 | — | x |
| Sample 6 Control | 4.9 | x | 83.0 | o | 0 | 320 | — | — | x |
| Sample 7 | | | | | | | | | |

Note 1: The weight ratios shown in the Table were obtained, as in Example 1, on the basis of the results shown in Table 1.
Note 2: In the items of "Evaluation" and "Overall Evaluation" shown in the Table, "o" indicates that the phosphatidylcholine fulfills the requirements of the present invention regarding the weight ratio among the molecular species and electric conductivity of the phosphatidylcholine of the present invention, and "x" indicates that the phosphatidylcholine does not fulfill these requirements. Further, "—" indicates that the measurement was discontinued because the result obtained was found to be clearly different from those obtained in Examples 1 and 2.

Examples of conventionally known phosphatidylcholines having the same weight ratio among the molecular species as that of the phosphatidylcholines of the present invention will be set forth in the following Reference Examples 1 and 2.

REFERENCE EXAMPLE 1

A yolk phosphatidylcholine was prepared in accordance with the method described in LIPIDS, 2 (3), 217–224 (1967). (The phosphatidylcholine thus prepared has a (PLPC+POPC)/(SLPC+SOPC) value of 2.9 as determined according to the table of the molecular species of yolk phosphatidylcholines shown on page 125 of "Lecithins" (1985) published by the American Oil Chemists' Society.)

The electric conductivity of the above-prepared sample was 270 μS/cm as measured in the same manner as in Example 1.

REFERENCE EXAMPLE 2

A yolk phosphatidylcholine was prepared in accordance with the method described in J. Biol. Chem., 188, 471–476 (1950). (The phosphatidylcholine thus prepared has the above defined weight ratio of 2.1 as determined according to the table on page 125 of the aforementioned "Lecithins".)

The electric conductivity of the above-prepared sample was 390 μS/cm as measured in the same manner as in Example 1.

INDUSTRIAL APPLICABILITY

The phosphatidylcholines of the present invention, without requiring any special treatment, are per se excellent in oxidation stability, and have eliminated the fundamental problems encountered in the application of the conventional phosphatidylcholines.

Therefore, the phosphatidylcholines of the present invention can be easily stored, and drugs, cosmetics, foods or the like can also be produced easily and stored stably by utilizing the phosphatidylcholines. In addition, the phosphatidylcholines are not susceptible to oxidation, so that it can be expected that stable drugs, cosmetics, foods or the like are produced by the use of the phosphatidylcholines.

We claim:

1. A phosphatidylcholine characterized in that the ratio of the total weight of palmitoyl-linoleoyl-glycerophosphocholine (PLPC) and palmitoyl-oleoyl-glycerophosphocholine (POPC) to the total weight of stearoyl-linoleoyl-glycerophosphocholine (SLPC) and stearoyl-oleoyl-glycerophosphocholine (SOPC) is 4.5 or less, the PLPC, POPC, SLPC and SOPC being molecular species constituting the phosphatidylcholine, and that the electric conductivity of a 5 wt. % suspension of the phosphatidylcholine in distilled water is 100 μS/cm or less.

2. A process for producing a phosphatidylcholine of claim 1, characterized in that a solvent mixture of an alcohol having 4 or less carbon atoms and water is used as a mobile phase solvent in the treatment of a lipid composition containing the phosphatidylcholine by liquid column chromatography, and that an eluate delivered after the point at which the chromatogram of the phosphatidylcholine fraction shows a maximum value is collected.

* * * * *